(12) United States Patent
Harel

(10) Patent No.: US 9,975,846 B2
(45) Date of Patent: May 22, 2018

(54) MULTIVALENT COMPOUNDS FOR USE IN THE TREATMENT AND PREVENTION OF BRAIN DAMAGE

(71) Applicant: MEDICORTEX FINLAND OY, Turku (FI)

(72) Inventor: Adrian Harel, Turku (FI)

(73) Assignee: MEDICORTEX FINLAND OY, Turku (FI)

(*) Notice: Subject to any disclaimer, the term of this patent is extended or adjusted under 35 U.S.C. 154(b) by 0 days. days.

(21) Appl. No.: 15/516,192

(22) PCT Filed: Oct. 2, 2015

(86) PCT No.: PCT/FI2015/050659
§ 371 (c)(1),
(2) Date: Mar. 31, 2017

(87) PCT Pub. No.: WO2016/051024
PCT Pub. Date: Apr. 7, 2016

(65) Prior Publication Data
US 2017/0298010 A1 Oct. 19, 2017

(30) Foreign Application Priority Data
Oct. 3, 2014 (FI) .................................... 20145861

(51) Int. Cl.
*C07C 235/64* (2006.01)
*C07C 233/44* (2006.01)

(52) U.S. Cl.
CPC .......... *C07C 235/64* (2013.01); *C07C 233/44* (2013.01)

(58) Field of Classification Search
CPC ................................................. C07C 235/64
See application file for complete search history.

(56) References Cited

U.S. PATENT DOCUMENTS 3,627,750 A * 12/1971 Ronco .................... C09B 33/147
106/31.81
2003/0236202 A1 12/2003 Geelings et al.
2011/0015272 A1 1/2011 Snow et al.

FOREIGN PATENT DOCUMENTS

WO WO-2013/158302 A1 10/2013

OTHER PUBLICATIONS

Farooqul et al., Inhibitors of brain phospholipase A2 activity: their neuropharmacological effects and therapeutic importance for the treatment of neurologic disorders, Pharmacol. Rev., 58(3):591-620 (2006).
International Preliminary Report on Patentability, International Application No. PCT/FI2015/050659, dated Apr. 4, 2017.
International Search Report and Written Opinion, International Patent Application No. PCT/FI2015/050659, dated Jan. 13, 2016.
Kawakita et al., Docosahexaenoic acid promotes neurogenesis in vitro and in vivo, Neuroscience, 139(3):991-7 (2006).
Kim et al., N-Docosahexaenoylethanolamide promotes development of hippocampal neurons, Biochem. J., 435(2):327-36 (2011).
McConeghy et al., A review of neuroprotection pharmacology and therapies in patients with acute traumatic brain injury, CNS Drugs, 26(7):613-36 (2012).
Opinion on Patentability, Finnish patent application No. 20145861, dated May 29, 2015.
Search Report, Finnish patent application No. 20145861, dated May 29, 2015.

* cited by examiner

*Primary Examiner* — Shawquia Jackson
(74) *Attorney, Agent, or Firm* — Marshall, Gerstein & Borun LLP

(57) ABSTRACT

The present invention relates to compounds of general formula (I)

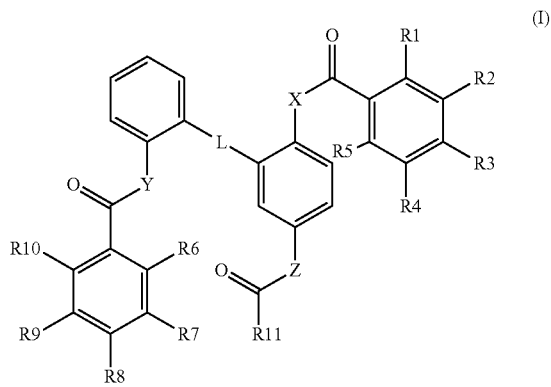

and pharmaceutically acceptable salts thereof;
wherein R1-R11, L, Z, Y, and Z are as defined in the claims. The invention also relates to said compounds for use as a medicament and particularly in the treatment of traumatic brain injury.

20 Claims, No Drawings

MULTIVALENT COMPOUNDS FOR USE IN THE TREATMENT AND PREVENTION OF BRAIN DAMAGE

FIELD OF THE INVENTION

The present disclosure relates to novel multivalent compounds and pharmaceutical compositions comprising them. The disclosure also relates to said compounds for use in the treatment and prevention of brain damage caused, for instance, by acute or chronic neurodegenerative conditions, particularly traumatic brain injury.

BACKGROUND OF THE INVENTION

Neurodegeneration, i.e. progressive loss of structure or function of neurons, is a major health and economic concern worldwide. Neurodegeneration may result from an acute brain injury or occur due to chronic neurodegeneration as in, for instance, Alzheimer's disease or Parkinson's disease. The process of neurodegeneration is not well-understood and, thus, no comprehensive cure is available, as yet.

Traumatic brain injury (TBI) is the leading cause of central nervous system impairment in these days. Some sources estimate that TBI is ten times as prevalent as spinal cord injury. For this reason it is often called the "silent epidemic". More than 1.7 million individuals suffer annually from TBI in the US alone. According to the CDC, the highest incidence of TBI occurs among children 0-4 years old, adolescents 15-19 years old, and adults over 65 years of age. Despite the broad range of the population affected, TBI is still under-served and remains an unexplored pathological condition.

Many drug candidates have entered clinical trials for the treatment of TBI over the past few decades, but nearly all have failed to prove efficacy in humans in large clinical studies.

There is thus an identified need for the development of novel therapeutics for the treatment of brain damage.

BRIEF DESCRIPTION OF THE INVENTION

The present invention relates to novel compounds of general formula (I)

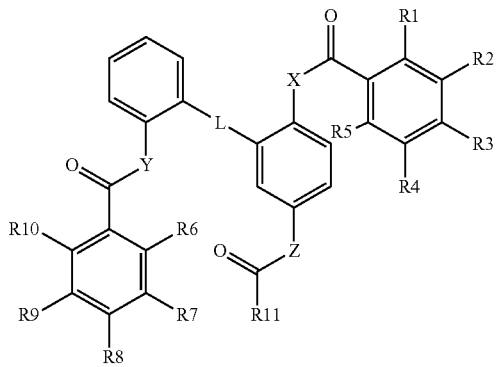

wherein
X and Y are each independently selected from NH, O and S;
Z is selected from NH, O and S;
R1 to R5 are each independently selected from H, OH, C1-3-alkyl, halogen, and C1-3-(per)haloalkyl, provided that at least two of R1 to R5 is OH;
R6 to R10 are each independently selected from H, OH, C1-3-alkyl, halogen, and C1-3-(per)haloalkyl, provided that at least two of R6 to R10 is OH;
L is a linker selected from a group consisting of $C_{1-10}$-alkylene, $C_{2-10}$-alkenylene and $C_{2-10}$-alkynylene, each of which is optionally interrupted one or more times with a group independently selected at each occurrence from the group consisting of —O—, —S—, —NH—, —C(=O)—, —C(=O)—O—, —C(=O)—NH—, —NH—C(=O)—NH—, NH—C(=O)—O—, —S(=O)—, —S(=O)—O—, and PO(=O)O—; and
R11 is $C_{10-25}$-alkenyl;
or a pharmaceutically acceptable salt thereof.

The invention also relates to a pharmaceutical composition comprising an effective amount of one or more compounds of formula (I) or pharmaceutically acceptable salts thereof, and a pharmaceutically acceptable carrier or excipient.

Further, the invention relates to compounds of formula (I) or pharmaceutically acceptable salts thereof for use as a medicament.

The invention also relates to compounds of formula (I) or pharmaceutically acceptable salts thereof for use in the treatment of brain damage.

Other objects, aspects, embodiments, details and advantages of the present invention will become apparent from dependent claims and the following detailed description and examples.

DETAILED DESCRIPTION OF THE INVENTION

The present invention relates to novel compounds having a general formula (I), and pharmaceutically acceptable salts thereof

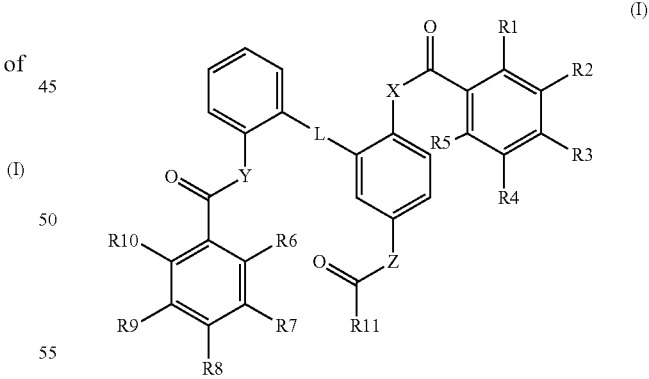

wherein
X and Y are each independently selected from NH, O and S;
Z is selected from NH, O and S;
R1 to R5 are each independently selected from H, halogen, OH, $C_{1-3}$-alkyl, $C_{1-3}$-(per)haloalkyl, and $C_{1-3}$-alkoxy, provided that at least two of R1 to R5 is selected independently from OH and $C_{1-3}$-alkoxy, such as methoxy;
R6 to R10 are each independently selected from H, halogen, OH, $C_{1-3}$-alkyl, $C_{1-3}$-(per)haloalkyl, and $C_{1-3}$- alkoxy, provided that at least two of R6 to R10 is selected independently from OH and $C_{1-3}$-alkoxy, such as methoxy, L is a linker selected from a group consisting of $C_{1-10}$-alkylene, $C_{2-10}$-alkenylene and $C_{2-10}$-alkynylene, each of which is optionally interrupted one or more times with a group independently selected at each occurrence from the group consisting of —O—, —S—, —NH—, —C(=O)—, —C(=O)—O—, —C(=O)—NH—, —NH—C(=O)—NH—, NH—C(=O)—O—, —S(=O)—, —S(=O)—O—, and PO(=O)O—; and R11 is $C_{10-25}$-alkenyl.

The term "comprise" as used herein and hereafter describes the constituents of the compositions of the present invention in a non-limiting manner i.e. the said composition comprising constituents consists of, at least, the said constituents, but may additionally, when desired, comprise other constituents. However, the said composition of the present invention comprising said constituents may consist of only the said constituents. The term "comprise" is further used to reflect that the composition of the present invention may comprise trace components of other materials or other impurities, or both, which do not alter the effectiveness or the safety of the mixture.

The term "alkyl" as used herein and hereafter as such or as part of haloalkyl, perhaloalkyl or alkoxy group is an aliphatic linear, branched or cyclic, especially linear or branched, hydrocarbon group having the indicated number of carbon atoms, for example $C_{1-3}$-alkyl has 1 to 3 carbon atoms in the alkyl moiety and thus, includes methyl, ethyl, n-propyl, isopropyl and cyclopropyl.

The term "haloalkyl" as used herein and hereafter refers to any of the above alkyl groups where one or more hydrogen atoms are replaced by halogen(s): in particular I, Br, F or Cl. Examples of haloalkyl groups include without limitation chloromethyl, fluoromethyl and —$CH_2CF_3$. The term "perhaloalkyl" is understood to refer to an alkyl group, in which all the hydrogen atoms are replaced by halogen atoms. Preferred examples include trifluoromethyl (—$CF_3$) and trichloromethyl (—$CCl_3$).

The term "$C_{1-3}$-alkoxy" as used herein and hereafter refers to a —O—($C_{1-3}$-alkyl) group where the "$C_{1-3}$-alkyl" has the above-defined meaning. Examples of preferred alkoxy groups include, but are not limited to, methoxy, ethoxy, and iso-propyloxy.

The term "$C_{1-10}$-alkylenyl" as used herein and hereafter, is a divalent linking alkyl group derived from a straight or branched chain saturated hydrocarbon having suitably 1 to 10, in particular 1 to 6, carbon atoms. Representative examples of alkylenyl include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "$C_{2-10}$-alkenylenyl" as used herein and hereafter, is a divalent linking alkenyl group derived from a straight or branched chain hydrocarbon having suitably 1 to 10, in particular 1 to 6, carbon atoms and one or more double bonds. Representative examples of alkenylenyl include, but are not limited to, —CH=CH—, —C($CH_3$)CH—, —CH=CHCH$_2$—, —$CH_2$CHCHCH$_2$—, —CHCHCH$_2$CH$_2$—, and —$CH_2$C($CH_3$)=CH—.

The term "$C_{2-10}$-alkynylenyl" as used herein and hereafter, is a divalent linking alkynyl group derived from a straight or branched chain hydrocarbon having suitably 1 to 10, in particular 1 to 6, carbon atoms and one or more triple bonds. Representative examples of alkenylenyl include, but are not limited to, —CC—, —CH($CH_3$)CC, —CCCH$_2$—, —$CH_2$CCCH$_2$—, —CCCH$_2$CH$_2$—, and —$CH_2$CCCH($CH_3$)—.

As used herein, the term "pharmaceutically acceptable" refers to qualities of being generally safe, non-toxic or otherwise undesirable for veterinary or human medicinal purposes.

Typical pharmaceutically acceptable salts include, but are not limited to, acid addition salts formed with inorganic acids, such as hydrochloric acid, hydrobromic acid, sulphuric acid, phosphoric acid, and the like, and salts formed with organic acids, such as acetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, salicylic acid, and the like. Pharmaceutically acceptable salts also include alkali metal salts, (e.g. sodium and potassium), alkaline earth metal salts (e.g. calcium or magnesium), aluminium salts, ammonium salts and salts with organic amines such as with methylamine, dimethylamine, trimethylamine, ethylamine, triethylamine, morpholine, and the like.

Pharmaceutically acceptable salts of the compounds of formula (I) may be prepared by conventional processes well-known to the person skilled in the art.

In a typical aspect of the present invention L is a linker selected from a group consisting of $C_{1-10}$-alkylene, $C_{2-10}$-alkenylene and $C_{2-10}$-alkynylene, each of which is optionally interrupted one, two or three times with a group selected from the group consisting of —O—, —O—, and —NH.

In particular the present invention provides compound of formula (I) having formula (I*)

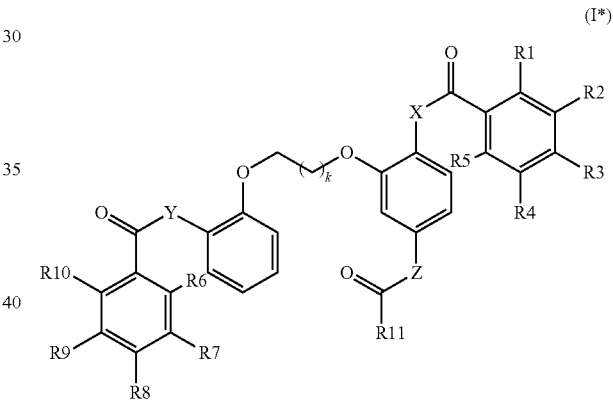

(I*)

wherein

X and Y are each independently selected from NH, O and S;

Z is selected from NH, O and S;

R1 to R5 are each independently selected from H, halogen, OH, $C_{1-3}$-alkyl, $C_{1-3}$-(per)haloalkyl, and $C_{1-3}$-alkoxy, provided that at least two of R1 to R5 is selected independently from OH and $C_{1-3}$-alkoxy, such as methoxy;

R6 to R10 are each independently selected from H, halogen, OH, $C_{1-3}$-alkyl, $C_{1-3}$-(per)haloalkyl, and $C_{1-3}$-alkoxy, provided that at least two of R6 to R10 is selected independently from OH and $C_{1-3}$-alkoxy, such as methoxy, k is an integer from 1 to 5; and R11 is $C_{10-25}$-alkenyl;

and pharmaceutically acceptable salts thereof.

In an aspect of the present invention at least two of R1 to R5 is OH, in particular R1 and R2 are each OH. In a further aspect of the present invention R3 to R5 are each H.

In an another aspect of the present invention at least two of R6 to R10 is OH, in particular R9 and R10 are each OH. In still a further aspect of the present invention R6 to R8 are each H.

In a preferred aspect of the present invention the compound of formula (I) is a compound of formula (Ia)

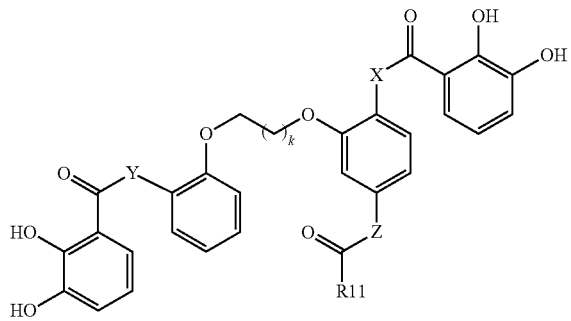

wherein
X and Y are each independently selected from NH, O and S;
Z is selected from NH, O and S;
k is an integer from 1 to 5; and
R11 is $C_{10-25}$-alkenyl;
or a pharmaceutically acceptable salt thereof.

In an advantageous aspect of the present invention X and Y are each independently NH or O. In a further advantageous aspect of the present invention Z is NH.

In a preferred aspect of the present invention X and Y are each independently NH or O; and Z is NH.

In a typical aspect of the present invention k is 1.

In preferable aspect of the present invention R11 is $C_{15-20}$-alkenyl.

Examples of particularly preferred specific compounds of formula (I) are:

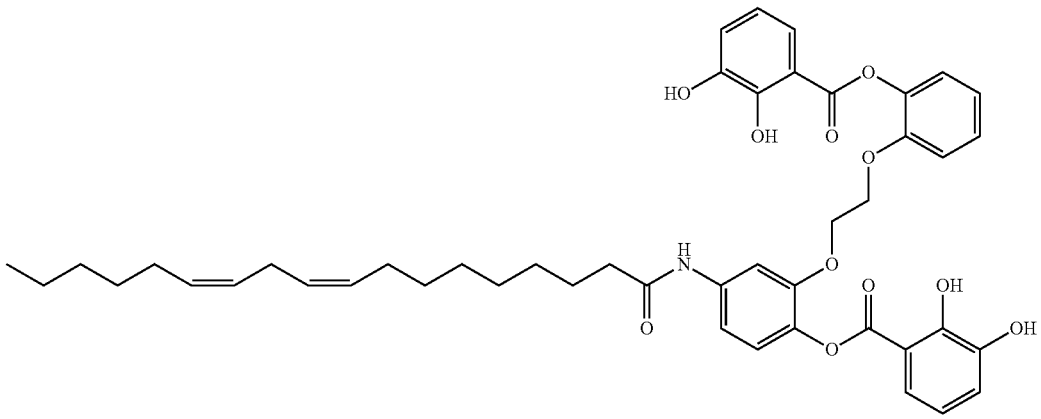 [SMILES: CCCCC/C=C\C/C=C\CCCCCCCC(=O)Nc1ccc(OC(=O)c2cccc(O)c2O)c(OCCOc2ccccc2OC(=O)c2cccc(O)c2O)c1]

2-(2-(2-((2,3-dihydroxybenzoyl)oxy)-5-((9Z,12Z)-octadeca-9,12-dienamido)phenoxy)ethoxy)phenyl 2,3-dihydroxybenzoate (called TBI-446); and

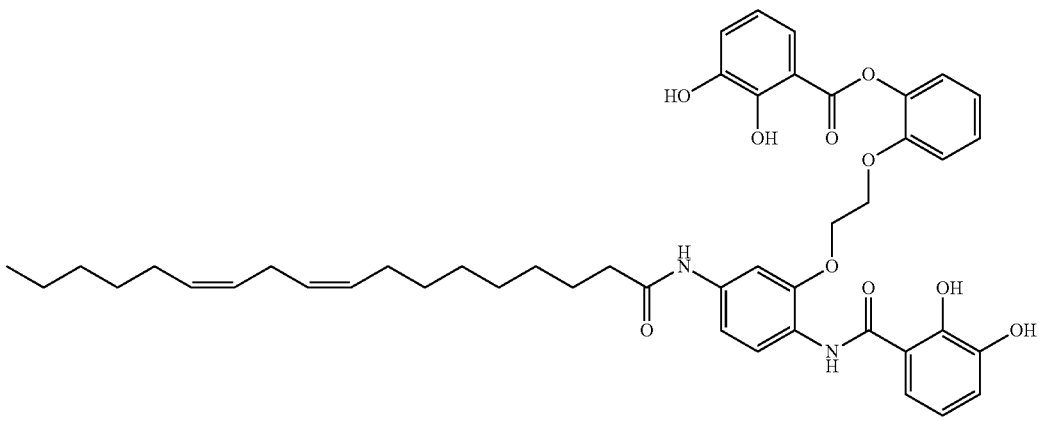

N-(2-(2-(2-(2,3-dihydroxybenzamido)-5-((9Z,12Z)-octadeca-9,12-dienamido)phenoxy)ethoxy)phenyl)-2,3-dihydroxybenzamide (called TBI-467);
and pharmaceutically acceptable salts thereof.
The compounds of the invention may be prepared by methods described below. For example the compounds of formula (I), where X, Y and Z are NH, may be prepared via the following reaction steps:
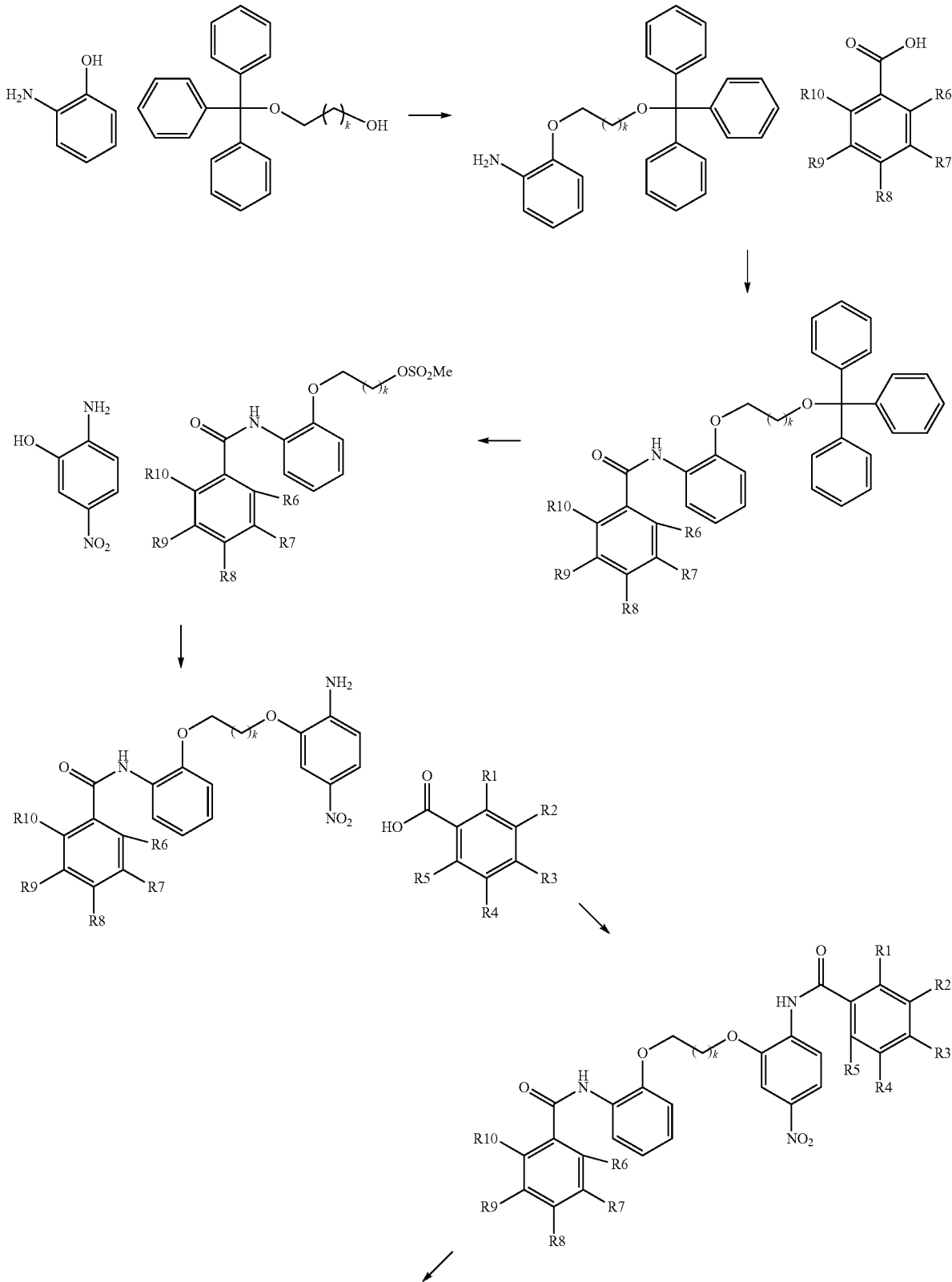

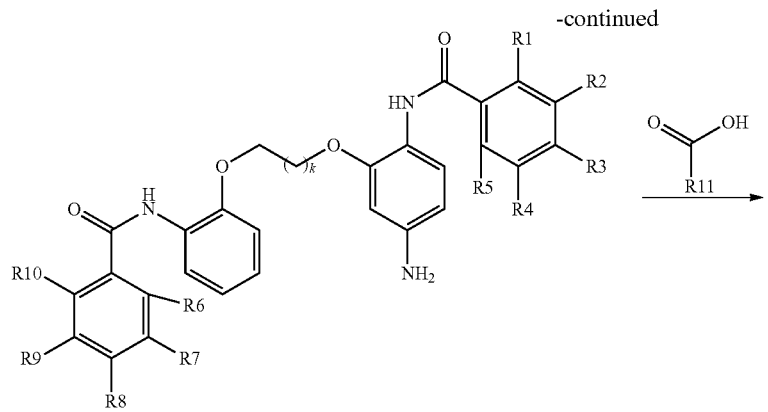

-continued

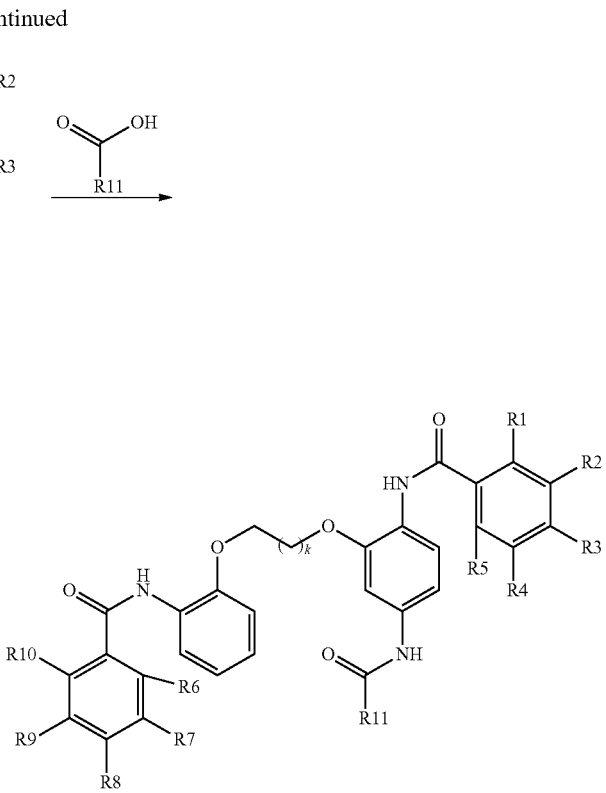

General Synthesis Procedure

General Method for the Synthesis of the Intermediate (3)

2-aminophenol dissolved in acetone is reacted with trityloxyalkanol in the presence of $K_2CO_3$. The reaction mixture is quenched and extracted. The organic phase is washed with water and dried over $Na_2SO_4$ and evaporated. Reaction gives intermediate (3).

General Method for the Synthesis of the Intermediate (5)

Intermediate (3) is dissolved in dichloromethane and reacted with a dimethoxybenzoic acid (4) in the presence of DCC. The reaction mixture is quenched and extracted. The organic phase is washed with water and dried over $Na_2SO_4$ and evaporated. Reaction gives intermediate (5).

General Method for the Synthesis of the Intermediate (6)

Intermediate is dissolved in methanol and the protecting group is cleaved in the presence of HCl. The reaction mixture is quenched and extracted. The organic phase is washed with water and dried over $Na_2SO_4$ and evaporated. Reaction gives alcohol (6a).

Alcohol (6a) is reacted $MeSO_2Cl$ in the presence of pyridine. The reaction mixture is quenched and extracted. The organic phase is washed with water and dried over $Na_2SO_4$ and evaporated. Reaction gives intermediate (6).

General Method for the Synthesis of the Intermediate (8)

Intermediate (6) is dissolved in acetone and reacted with 2-amino-5-nitrophenol (7) in the presence of $K_2CO_3$. The reaction mixture is quenched and extracted. The organic phase is washed with water and dried over $Na_2SO_4$ and evaporated. Reaction gives intermediate (8).

General Method for the Synthesis of the Intermediate (10)

Intermediate (8) is dissolved in dichloromethane and reacted with a dimethoxybenzoic acid (9). The reaction mixture is quenched and extracted. The organic phase is washed with water and dried over $Na_2SO_4$ and evaporated. Reaction gives intermediate (10).

General Method for the Synthesis of the Intermediate (11)

Intermediate (10) is reacted with hydrogen in the presence of Pd/C and $(NH_4)_2CO_3$. The reaction mixture is quenched and extracted. The organic phase is washed with water and dried over $Na_2SO_4$ and evaporated. Reaction gives intermediate (11).

General Method for the Synthesis of the Intermediate (13)

Intermediate (11) is dissolved in dichloromethane and reacted with an alkenoic acid (12) in the presence of DCC. The organic phase is washed with water and dried over $Na_2SO_4$ and evaporated. Reaction gives intermediate (13).

General Method for the Synthesis of the Compound of Formula (I)

Intermediate 13 is dissolved in dichloromethane and reacted with $BBr_3$ to cleave protective groups. The organic phase is washed with water and dried over $Na_2SO_4$ and evaporated. Reaction gives compound of formula (I).

Pharmaceutical Compostions

The present invention further provides a pharmaceutical composition comprising a pharmaceutically acceptable carrier, vehicle, or excipient and, as active ingredient a compound of formula (I). Said compound is present in an amount fully or partially effective for the desired purpose, such as prophylactic, palliative, or preventive purpose, or for curing brain damage, or any symptoms thereof in human or animal subjects. In some embodiments, the pharmaceutical composition may comprise one or more compounds of formula (I).

As used herein, the term "brain damage" refers to the destruction or degeneration of brain cells due to one or more internal or external factors. Non-limiting examples of brain damage include traumatic brain injury (TBI), acquired brain injury (ABI), and neurodegenerative conditions. As used herein, the terms "brain damage" and "brain injury" are interchangeable, unless otherwise indicated.

As used herein, the term "traumatic brain injury" (TBI) refers brain injury caused by external physical trauma. Non-limiting examples of incidences resulting in TBI include falls, vehicle collisions, sports collisions, and combats. The term includes both mild and severe TBI including closed-head injuries, concussions or contusions and penetrating head injuries.

As used herein, the term "acquired brain injury" (ABI) refers to a brain damage not caused by an external brain injury. ABI may occurring after birth as a result of to a disorder or congenital malady, or it may result from, for instance, stroke, surgery, brain tumour, infection, chemical and/or toxic poisoning, hypoxia, ischemia, substance abuse, or a combination thereof.

As used herein, the term "neurodegenerative condition" refers to an incurable and debilitating condition which results in progressive degeneration and/or death of nerve cells. Symptoms of neurodegeneration include, but are not limited to, problems with movement (called ataxias) or mental functioning (called dementias). Non-limiting examples of neurodegenerative conditions include Alzheimer's Disease and other dementias, Parkinson's Disease (PD) and PD-related disorders, Huntington's Disease, Multiple System Atrophy (MSA), and Amyotrophic Lateral Sclerosis (ALS).

In some embodiments, the pharmaceutical composition comprises a compound of (I) within the dosage range of about 0.01 mg/kg to about 1000 mg/kg, more preferably about 0.1 mg/kg to about 100 mg/kg, and even more preferably about 1 mg/kg to about 10 mg/kg. The compounds of formula (I) may be administered in a single daily dose, or the total daily dosage may be administered in divided doses, e.g. of two, three or four times daily.

The pharmaceutical composition may be administered by any appropriate route of administration, including but not limited to, intravenous (i.v.), intramuscular (i.m.), intraperitoneal (i.p), subcutaneous (s.c), intra-arterial, transdermal, topical, intranasal, sublingual, and oral administration. Depending on the administration route, the pharmaceutical composition may have a form selected from solutions, dispersions, suspensions, powders, capsules, tablets, pills, controlled release capsules, controlled release tablets, and controlled release pills, for instance.

The pharmaceutical composition may comprise aqueous or non-aqueous solvents, co-solvents, solubilizers, dispersing or wetting agents, suspending agents and/or viscosity agents, as needed. Non-limiting examples of non-aqueous solvents are propylene glycol, polyethylene glycol, vegetable oil, fish oil, and injectable organic esters. Aqueous carriers include, for instance, water, water-alcohol solutions, including saline and buffered medial parenteral vehicles including sodium chloride solution, Ringer's dextrose solution, dextrose plus sodium chloride solution, Ringer's solution containing lactose, or fixed oils. Non-limiting examples of intravenous vehicles include fluid and nutrient replenishers, electrolyte replenishers, such as those based on Ringer's dextrose and the like. Aqueous compositions may comprise suitable buffer agents, such as sodium and potassium phosphates, citrate, acetate, carbonate or glycine buffers depending on the targeted pH-range. The use of sodium chloride as a tonicity adjuster is also useful. The compositions may also include other excipients, such as stabilizing agents or preservatives. Useful stabilizing excipients include surfactants (polysorbate 20 & 80, poloxamer 407), polymers (polyethylene glycols, povidones), carbohydrates (sucrose, mannitol, glucose, lactose), alcohols (sorbitol, glycerol propylene glycol, ethylene glycol), suitable proteins (albumin), suitable amino acids (glycine, glutamic acid), fatty acids (ethanolamine), antioxidants (ascorbic acid, cysteine etc.), chelating agents (EDTA salts, histidine, aspartic acid) or metal ions (Ca, Ni, Mg, Mn). Among useful preservative agents are benzyl alcohol, chlorbutanol, benzalkonium chloride and possibly parabens.

In solid dosage forms, compounds of formula (I) may be admixed with at least one inert diluent such as sucrose, lactose or starch. Such dosage forms may also comprise, as is normal practice, pharmaceutical adjuvant substances, e.g. stearate lubricating agents or flavouring agents. Solid oral preparations can also be prepared with enteric or other coatings which modulate release of the active ingredients.

Non-limiting examples of liquid dosage forms for oral administration include pharmaceutically acceptable emulsions, solutions, suspensions, syrups and elixirs containing inert non-toxic diluents commonly used in the art, such as water and alcohol. Such compositions may also comprise adjuvants, such as wetting agents, buffers, emulsifying, suspending, sweetening and flavouring agents.

The pharmaceutical composition may be provided in a concentrated form or in a form of a powder to be reconstituted on demand. In case of lyophilizing, certain cryoprotectants are preferred, including polymers (povidones, polyethylene glycol, dextran), sugars (sucrose, glucose, lactose), amino acids (glycine, arginine, glutamic acid) and albumin. If solution for reconstitution is added to the packaging, it may consist e.g., of sterile water for injection or sodium chloride solution or dextrose or glucose solutions.

The pharmaceutical compositions of the present invention can be manufactured in a manner which is in itself known, for example, by means of conventional mixing, granulating, dragee-making, dissolving, lyophilizing or similar processes.

Therapeutic Use

The present pharmaceutical compositions comprising compounds of formula (I) may be used for the treatment of various forms of brain damage including, but not limited to, TBI due to closed-head injuries, concussion or contusions and penetrating head injury. The compositions can also be used for protecting the brain before, during or after an activity associated with a potential traumatic brain injuring event such as contact sport, armed conflict or brain surgery.

The term "primary brain injury" refers to the damage caused at the moment of injury, whereas the term "secondary brain injury," refers to a variety of events that take place in the minutes and days following the injury. These processes, which include inflammation, oxidative stress, ionic imbalance, increased vascular permeability, and damage to the blood-brain barrier, contribute substantially to the damage from the initial injury.

In some embodiments, the present compounds are particularly efficient in the treatment of secondary brain injuries because they are able to, for instance, cross the blood-brain barrier (BBB), bind free metals, prevent oxidative stress, inflammation or infections, or provide an energy source for mitochondria. As a result of these beneficial effects, the cascade of events leading to brain degeneration upon secondary brain injury can potentially be halted. In some embodiments, the present compounds have at least two of these beneficial effects.

According to some more specific embodiments, the present compounds have the ability to cross the BBB owing to a penetrating head/tail R11. Alternatively or additionally, the present compounds may function as an energy source for mitochondria. This is a beneficial property because the imbalance between a higher energy demand for repair of cell damage and decreased energy production caused by mitochondrial damage aggravates the secondary brain injury.

As used herein, the term "treatment" or "treating" refers not only to complete cure of brain damage, but also to prevention, alleviation, and amelioration of the brain damage or symptoms related thereto.

As used herein, the term "subject" refers to an animal or human subject. Non-limiting examples of typical human subjects suffering from or pre-disposed to brain damage, TBI in particular, include children and young adults, particularly male; elderly; athletes, particularly boxers, ice-hockey players, soccer players, and skateboarders); and soldiers.

Amounts and regimens for the therapeutic use of the present compounds can be determined readily by those with ordinary skill in the clinical art of treating head injuries. Generally, the treatment schedule will depend upon the severity of the brain damage and other considerations such as: age, gender and general health of the patient to be treated; kind of concurrent treatment, if any; frequency of treatment and nature of the effect desired; extent of tissue damage; duration of the symptoms; and other variables to be adjusted by the individual physician. The schedule can also vary depending on whether it is to be administered in a veterinary setting to an animal or to a human patient.

In accordance with the above, one aspect of the present invention provides a method for preventing or treating a brain damage by administering to a subject in need thereof an effective amount of a compound of formula (I). In some embodiments, the compound is administered in a pharmaceutical composition.

According to another aspect, the present invention relates to the use of a compound of formula (I), or a pharmaceutical composition comprising such compound, in the manufacture of a medicament for the prevention or treatment of a brain damage.

According to yet another aspect, the present invention relates to a compound of formula (I), or a pharmaceutical composition comprising such compound, for use in the prevention or treatment of a brain damage.

It will be obvious to a person skilled in the art that, as the technology advances, the inventive concept can be implemented in various ways. The invention and its embodiments are not limited to the examples described above but may vary within the scope of the claims.

EXAMPLES

All animal experiments are carried out according to institutional guidelines that are in compliance with national and international laws for the care and use of laboratory animals, and under approval by national Ethical Committee.

Example 1. Effects of the Present Compounds on Cognitive Rehabilitation after Traumatic Brain Injury A mouse model of experimental closed head injury disclosed by Yatsiv et al. in FASEB J. 2005, 19:1701-1703 is employed for testing the efficacy of the present compounds to improve functional recovery after a head trauma caused by a weight-drop onto an exposed skull.

Severity of the injury is assessed according to the Neurological Severity Score disclosed by Beni-Adani et al. (J. Pharmacol. Exp. Ther. 2001, 296:57-63) on the basis of ten individual tasks reflecting motor function, alertness, and behaviour. Severity assessment is carried out 1 hour and 7 days after the trauma in order to allocate the mice into comparable study groups.

Each test compound, control compound, or vehicle is administered subcutaneously from day 8 onwards, three times a week.

Behavioral tests, including open field (OF), elevated plus maze (EMP), and social recognition tests are carried out at baseline, on day 7, and day 30.

After euthanization, plasma levels of cytokines and TBI-specific biomarkers, such as S100B, are determined and the brains are evaluated histologically.

Treatment with the present compounds, TBI-446 and TBI-467 in particular, results in improved cognitive rehabilitation of the mice.

Example 2. Effects of the Present Compounds on Behaviour, Brain Edema and Lesion Volume after Traumatic Brain Injury A rat model of experimental closed head injury disclosed by Bilgen et al. (Neurorehabil. Neural Repair, 2005, 19:219-226) with some modifications is employed for testing the effect of the present compounds on behaviour, brain edema, lesion volume, and inflammatory markers after a head trauma.

Each test compound, control compound, or vehicle is administered orally 6 h post-injury.

In vivo T2 weighted magnetic resonance imaging (MRI) is performed on the animals to depict the pathologies, including lesion size, tissue viability, and brain edema, of the resulting injuries in the corresponding neuronal tissues at 24 h and day 3.

Behavioral tests, including a seven-point neuroscore test modified from Zausinger et al. (Brain Res., 2000, 863:94-105), are used to assess motor and behavioural deficits by a blinded investigator at baseline and on days 1, 3, 7, 14, and 28 post-injury. Additionally, sensimotor recovery of forelimb and hindlimb responses to tactile and proprioceptive stimulation is evaluated by a limb-placing test essentially as described by Jolkkonen et al. in Restor. Neurol. Neurosci., 2000, 17:211-216.

After euthanization, histological evaluation of the injury in the cortex and hippocampus is performed. Additionally, inflammatory markers, astrocytic and microglial activation is evaluated by immunohistochemistry.

Treatment with the present compounds, TBI-446 and TBI-467 in particular, results in behavioural recovery, and decreased brain edema and lesion volume after closed head injury. Furthermore, levels of inflammatory markers are decreased.

Example 3. Effects of the Present Compounds on Dopaminergic System Protection in a Parkinson's Model The well-established MPTP mouse model of Parkinson's disease is employed for testing the effects of the present compounds in dopaminergic system protection.

In the model, depletion of striatal dopamine (DA) and dopaminergic neuronal death in the substantia nigra (SN) is caused by systemic administration of MPTP (1-methyl-4-phenyl-1,2,3,6-tetrahydropyridine). To be more specific, MPTP is administered twice daily, 3 hours apart, by i.p. injections on Day 0 and Day 1. Each dose is 15 mg/kg, the total dose being 60 mg/kg.

Each test compound, control or vehicle is administered by daily i.p. injections for 14 days starting from Day 0.

After euthanization on Day 14, blood samples are collected by cardiac punctures and stored at −80° C. for further analysis. Blood is removed from the brains by transcardial perfusion with saline. Posterior brain blocks containing the SN are then removed and processed for cryosectioning, while striata are dissected in toto, pooled, weighted, snap-frozen in liquid nitrogen, and stored at −80° C.

20-μm-thick coronal cryosections are analysed immunohistochemically for the expression of tyrosine hydroxylase (TH), a rate-limiting enzyme in dopamine synthesis by counting the number of TH-positive neurons bilaterally in the SN. In control animals, a significant loss of TH-positive neurons is detected, while treatment with the present compounds inhibits said loss.

Striatal tissue samples are analysed for DA and its two metabolites, 3,4-dihydroxyphenylacetic acid (DOPAC) and homovanillic acid (HVA), levels by HPLC. The results show that the present compounds, TBI-446 and TBI-467 in particular, protect the dopaminergic system from the reduction of the DA levels cause by MPTP.

Example 4. Effects of the Present Compounds on Dopaminergic System Protection and Behavioral Skills in a Parkinson's Model The MPTP model of Example 3, with some modifications, is employed for testing the effects of the present compounds in dopaminergic system protection and behavioral skills.

In this administration scheme, mice are injected i.p. four times with a MPTP dose of 10 mg/kg, two hours apart, on Day 1. Each test compound, control and vehicle are administered s.c. three times a week from Day 2 until Day 21. The present compounds are administered either alone or in combination with a non-steroidal anti-inflammatory drug, antioxidant, and/or metal ions chelate.

One week prior to the MPTP dosing, the mice are trained for a rotarod performance test for three days. The rotarod test is then repeated four times during the course of the experiment. Motor performance and coordination is also tested by a pole test. Social recognition test is conducted once on the last days of the experiment.

Effects of the test compounds on the dopaminergic system protection are determined as described in Example 3.

Treatment with the present compounds, TBI-446 and TBI-467 in particular, results in behavioural recovery and dopaminergic system protection.

The invention claimed is:

1. A compound of formula (I)

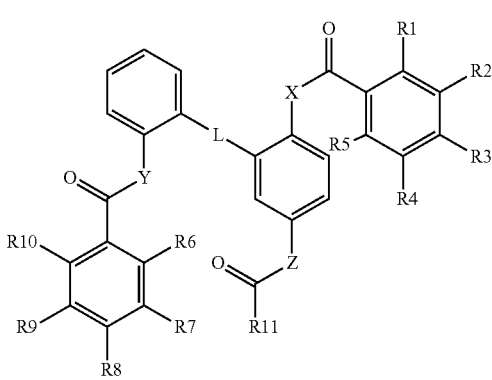

(I)

wherein

X and Y are each independently selected from NH, O and S;

Z is selected from NH, O and S;

R1 to R5 are each independently selected from H, halogen, OH, $C_{1-3}$-alkyl, $C_{1-3}$-(per)haloalkyl, and $C_{1-3}$-alkoxy, provided that at least two of R1 to R5 is selected independently from OH and $C_{1-3}$-alkoxy;

R6 to R10 are each independently selected from H, halogen, OH, $C_{1-3}$-alkyl, $C_{1-3}$-(per)haloalkyl, and $C_{1-3}$-alkoxy, provided that at least two of R6 to R10 is selected independently from OH and $C_{1-3}$-alkoxy, L is a linker selected from a group consisting of $C_{1-10}$-alkylenyl, $C_{2-10}$-alkenylenyl and $C_{2-10}$-alkynylenyl, each of which is optionally interrupted one or more times with a group independently selected at each occurrence from the group consisting of —O—, —S—, —NH—, —C(=O)—, —C(=O)—O—, —C(=O)—NH—, —NH—C(=O)—NH—, NH—C(=O)—O—, —S(=O)—, —S(=O)—O—, and PO(=O)O—; and R11 is $C_{10-25}$-alkenyl;

or a pharmaceutically acceptable salt thereof.

2. A compound or salt as claimed in claim 1, wherein L is a linker selected from a group consisting of $C_{1-10}$-alkylene, $C_{2-10}$-alkenylene and $C_{2-10}$-alkynylene, each of which is optionally interrupted one, two or three times with a group selected from the group consisting of —O—, —S—, and —NH—.

3. A compound of formula (I) as claimed in claim 1, having formula (I*)

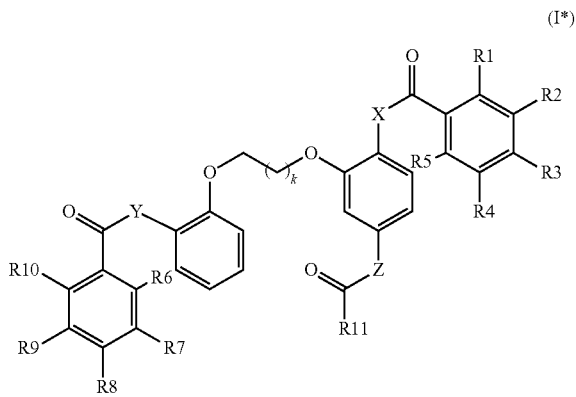

(I*)

wherein

X and Y are each independently selected from NH, O and S;

Z is selected from NH, O and S;

R1 to R5 are each independently selected from H, halogen, OH, $C_{1-3}$-alkyl, $C_{1-3}$-(per)haloalkyl, and $C_{1-3}$-alkoxy, provided that at least two of R1 to R5 is selected independently from OH and $C_{1-3}$-alkoxy;

R6 to R10 are each independently selected from H, halogen, OH, $C_{1-3}$-alkyl, $C_{1-3}$-(per)haloalkyl, and $C_{1-3}$-alkoxy, provided that at least two of R6 to R10 is selected independently from OH and $C_{1-3}$-alkoxy, k is an integer from 1 to 5; and R11 is $C_{10-25}$-alkenyl;

or a pharmaceutically acceptable salt thereof.

4. A compound or salt as claimed in claim 1, wherein at least two of R1 to R5 is OH.

5. A compound or salt as claimed in claim 1, wherein R1 and R2 are each OH.

6. A compound or salt as claimed in claim 5, wherein R3 to R5 are each H.

7. A compound or salt as claimed in claim 1, at least two of R6 to R10 is OH.

8. A compound or salt as claimed in claim 1, wherein R9 and R10 are each OH.

9. A compound or salt as claimed in claim 8, wherein R6 to R8 are each H.

10. A compound as claimed in claim 1, having formula (Ia)

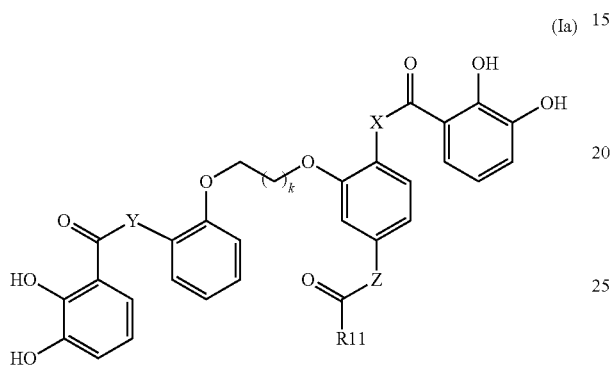

wherein
X and Y are each independently selected from NH, O and S;
Z is selected from NH, O and S;
k is an integer from 1 to 5; and
R11 is $C_{10-25}$-alkenyl;
or a pharmaceutically acceptable salt thereof.

11. A compound or salt as claimed in claim 1, wherein X and Y are each independently NH or O.

12. A compound or salt as claimed in claim 1, wherein Z is NH.

13. A compound or salt as claimed in claim 1, wherein X and Y are each independently NH or O; and
Z is NH.

14. A compound or salt as claimed in claim 1, wherein R11 is $C_{15-20}$-alkenyl.

15. A compound or salt as claimed in claim 3, wherein k is 1.

16. A compound as claimed in claim 1, selected from:
2-(2-(2-((2,3-dihydroxybenzoyl)oxy)-5-((9Z,12Z)-octadeca-9,12-dienamido)phenoxy)ethoxy)phenyl 2,3-dihydroxybenzoate; and
N-(2-(2-(2-(2,3-dihydroxybenzamido)-5-((9Z,12Z)-octadeca-9,12-dienamido)phenoxy)ethoxy)phenyl)-2,3-dihydroxybenzamide;
or a pharmaceutically acceptable salt thereof.

17. A pharmaceutical composition comprising a compound or salt according to claim 1, and a pharmaceutically acceptable carrier, vehicle, or diluent.

18. A method of treating brain damage comprising administering the compound or pharmaceutically acceptable salt of claim 1 to a patient in need thereof.

19. The method of claim 18, wherein the compound or pharmaceutically acceptable salt is formulated as a solution, dispersion, suspension, powder, capsule, tablet, or pill.

20. The method of claim 18, wherein the brain damage is the result of a traumatic brain injury, an acquired brain injury, or a condition selected from the group consisting of Alzheimer's Disease or another dementia, Parkinson's Disease or a Parkinson's Disease-related disorder, Huntington's Disease, Multiple System Atrophy, and Amyotrophic Lateral Sclerosis.

* * * * *